United States Patent
Spleiss

(10) Patent No.: US 10,314,789 B2
(45) Date of Patent: Jun. 11, 2019

(54) SOFT GELATIN ENCAPSULATED PHARMACEUTICAL COMPOSITION OF CIS-5,8,11,14,17-EICOSAPENTAENOIC ACID IN FREE ACID FORM AND CIS-7,10,13,16,19-DOCOSAPENTAENOIC ACID IN FREE ACID FORM

(71) Applicant: Chrysalis Pharma AG, Sachsein (CH)

(72) Inventor: Johannes Spleiss, Ziefen (CH)

(73) Assignee: Chrysalis Pharma AG, Sachseln (CH)

( * ) Notice: Subject to any disclaimer, the term of this patent is extended or adjusted under 35 U.S.C. 154(b) by 0 days.

(21) Appl. No.: 14/427,846

(22) PCT Filed: Sep. 6, 2013

(86) PCT No.: PCT/EP2013/068488
§ 371 (c)(1),
(2) Date: Mar. 12, 2015

(87) PCT Pub. No.: WO2014/040921
PCT Pub. Date: Mar. 20, 2014

(65) Prior Publication Data
US 2015/0297529 A1  Oct. 22, 2015

(30) Foreign Application Priority Data
Sep. 13, 2012 (GB) .................................. 1216385.3

(51) Int. Cl.
| | | |
|---|---|---|
| *A61K 9/48* | (2006.01) | |
| *A61K 31/202* | (2006.01) | |
| *A61K 31/201* | (2006.01) | |
| *A61K 45/00* | (2006.01) | |
| *A61P 25/18* | (2006.01) | |
| *A61P 29/00* | (2006.01) | |
| *A61P 3/06* | (2006.01) | |
| *A61P 11/06* | (2006.01) | |

(52) U.S. Cl.
CPC .......... *A61K 9/4825* (2013.01); *A61K 9/4833* (2013.01); *A61K 9/4866* (2013.01); *A61K 9/4891* (2013.01); *A61K 31/202* (2013.01)

(58) Field of Classification Search
None
See application file for complete search history.

(56) References Cited

U.S. PATENT DOCUMENTS

| | | | |
|---|---|---|---|
| 2,870,062 | A | 1/1959 | Stanley et al. |
| 5,043,328 | A | 8/1991 | Weithmann |
| 5,874,470 | A | 2/1999 | Nehne et al. |
| 6,234,464 | B1 | 5/2001 | Krumbholz et al. |
| 7,960,370 | B2 | 6/2011 | Sachetto et al. |
| 9,050,308 | B2 | 6/2015 | Maines et al. |
| 2007/0269507 | A1 | 11/2007 | Sachetto et al. |
| 2010/0062057 | A1 | 3/2010 | Berge et al. |
| 2011/0097394 | A1 | 4/2011 | Sachetto et al. |
| 2011/0262534 | A1 | 10/2011 | Berge et al. |
| 2013/0123362 | A1 | 5/2013 | Sachetto et al. |
| 2013/0177643 | A1 | 7/2013 | Maines et al. |
| 2013/0209556 | A1 | 8/2013 | Maines et al. |

FOREIGN PATENT DOCUMENTS

| | | | |
|---|---|---|---|
| DE | 19956400 A1 * | 6/2001 | ............. A61K 31/20 |
| EP | 0 100 052 | 2/1984 | |
| EP | 0 244 832 | 11/1987 | |
| EP | 0 289 204 | 11/1988 | |
| EP | 0 311 091 | 4/1989 | |
| WO | 93/21912 | 11/1993 | |
| WO | 96/36329 | 11/1996 | |
| WO | 2005 079853 | 9/2005 | |
| WO | 2010 029433 | 3/2010 | |
| WO | 2012 112520 | 8/2012 | |
| WO | 2013 093630 | 6/2013 | |
| WO | 2013 103902 | 7/2013 | |

OTHER PUBLICATIONS

HMDB, metabocard for Docosapentaenoic acid, obtained online at: http://www.hmdb.ca/metabolites/HMDB06528, downloaded on Dec. 28, 2016.*
Holub, B.J. Clinical nutrition: 4. Omega-3 fatty acids in cardiovascular care. CMAJ. 166: 608-615, 2002.*
Remington, The Science and Practice of Pharmacy, 21st Edition, 2005, p. 918.*
Robinson et al., J. Pharm. Pharmac., 1975, 27, 818-824.*
Written Opinion of the International Searching Authority dated Nov. 6, 2013 in PCT/EP13/068488 Filed Sep. 6, 2013.
International Search Report dated Nov. 6, 2013 in PCT/EP13/068488 Filed Sep. 6, 2013.
Ωmthera Pharmaceutical Clinical Development Epanova Drug Product Stability Analysis Report—publically available after Sep. 13, 2012, 36 pp.
"*Gelatin Processing*," National Organic Standards Board Technical Advisory Panel Review Compiled by Organic Materials Review Institute for the USDA National Organic Program, Mar. 1, 2002, 25 pages.

* cited by examiner

*Primary Examiner* — Abigail Vanhorn
(74) *Attorney, Agent, or Firm* — Grüneberg and Myers PLLC

(57) ABSTRACT

Shelf life of soft gelatin capsules comprising a soft gelatin shell encapsulating a pharmaceutical formulation comprising cis-5,8,11,14,17-eicosapentaenoic acid (C20:5 n-3; "EPA") in free acid form in an amount from 25 wt % to 99 wt % of the formulation and cis-7,10,13,16,19-docosapentaenoic acid (C22:5 n-3; "DPA") in free acid form in an amount from 1 wt % to 75 wt % of the formulation in which the gelatin component of the shell is Type B gelatin, is improved by replacing up to 75 wt % of the gelatin component with porcine Type A gelatin.

11 Claims, No Drawings

SOFT GELATIN ENCAPSULATED PHARMACEUTICAL COMPOSITION OF CIS-5,8,11,14,17-EICOSAPENTAENOIC ACID IN FREE ACID FORM AND CIS-7,10,13,16,19-DOCOSAPENTAENOIC ACID IN FREE ACID FORM

The present invention relates generally to soft gelatin capsules and, in particular, soft gelatin capsules containing a pharmaceutical formulation comprising omega-3 polyunsaturated fatty acids in free acid form for use in the treatment of a variety of conditions including chronic inflammatory conditions; dyslipidaemia; hypertriglyceridaemia; asthma; bipolar disorder and neoplastic disease. The soft gelatin capsules have particular application in the treatment of "moderate" hypertriglyceridaemia in humans, i.e. humans having a blood plasma triglyceride level from about 200 to about 500 mg/dl, who are also on statin therapy, or "severe" hypertriglyceridaemia in humans, i.e. humans having a blood plasma triglyceride level of at least 500 mg/dl.

Gelatin is a heterogeneous mixture of water-soluble proteins of high molecular weight extracted from a number of sources of collagen such bovine bones and hide, pig skin or fish skin. Broadly speaking, there are two types of gelatin, Type A gelatin and Type B gelatin, depending on the method of extraction.

According to "Gelatin Processing" (US National Organic Standards Board Technical Advisory Panel Review; 1 Mar. 2002), Type A gelatin is extracted following an acid pre-treatment process and porcine gelatin is usually (but not necessarily) extracted in this way. Where porcine gelatin is from pigskin, the pigskins are typically dehaired and degreased and the resultant skin is passed through a chopper or macerator to cut the skin into uniform sizes. The skin is then soaked at a pH of 1 to 4 with a food-grade mineral acid such as hydrochloric acid, phosphoric acid or sulphuric acid for 8 to 30 hours. The acid-treated pigskin is then washed with water to remove impurities and extracted with hot water. The extract is filtered through an anion-cation exchange column to reduce ash or mineral levels. The gelatin extract is vacuum concentrated or ultra filtered to a concentration between 15 to 35%, filtered, pH adjusted to between 3.5 and 6, and evaporated to 50% solids. The residue is chilled, extruded, dried and milled to the required particle size and then packaged. Bovine Type A gelatin and fish Type A gelatin are also known.

Type B gelatin is extracted following an alkali pre-treatment process and bovine gelatin is usually extracted in this way (ibid). Bones are crushed, cooked, centrifuged and dried. The extracted bone is degreased prior to gelatin extraction and de-mineralised with 4 to 6% hydrochloric acid for a period of 5 to 7 days. The ossein is washed repeatedly with water to remove impurities and then treated with 1 to 4% lime (calcium hydroxide) slurry to adjust the pH to about 12 for periods of 35 to 70 days with agitation and weekly lime changes to remove non-collagen components. The ossein is then washed and mineral acid is added to neutralise excess lime and adjust the pH to 3. The final pH after all wash operations is between 5 and 7. De-mineralised hot water is then used to extract the gelatin. The liquid gelatin solution may be filtered through a cellulose/diatomaceous earth plate and frame filter and deionised using an anionic-cationic resin bed. The resin solution is evaporated to a concentration between 15 to 45%. The concentrated gelatin is filtered, pH adjusted to between 5 and 7, sterilised, cooled and air-dried. It is then milled to the required size and packaged. The alkaline process may take up to 20 weeks.

Gelatin is used, for example, to encapsulate various foods and nutritional supplements but especially medicines for oral administration of pharmaceutical formulations. Plasticizers such as glycerine may be added to gelatin to produce soft gelatin capsules. Formaldehyde and other aldehydes may be used to harden gelatin capsules and enable them to pass from the stomach to the intestines. The vast majority of soft gelatin capsules are manufactured from Type B gelatin, in particular bovine Type B gelatin.

Omega-3 (i.e. "ω-3" or "n-3") polyunsaturated fatty acids such as cis-5,8,11,14,17-eicosapentaenoic acid (C20:5 n-3; "EPA" also known as timnodonic acid) or cis-4,7,10,13,16, 19-docosahexaenoic acid (C22:6 n-3; "DHA" also known as cervonic acid) are well known to be useful in the treatment of inflammatory bowel disease (or "IBD") (see, for example, EP0244832A; EP0289204A; EP0311091; and WO93/21912A, the disclosures of which are incorporated herein by reference).

WO96/36329A (Buser et al; published on 21 Nov. 1996) exemplifies hard gelatin capsules containing a fatty acid formulation ("Purepa") derived from fish oil that comprises 42.4 wt % EPA in free acid form and 19.9 wt % DHA in free acid form. The formulation also contains other free fatty acids including 0.5 wt % "C22:5" which is a docosapentaenoic acid. The reference does not specify whether the C22:5 fatty acid is an omega-3 or omega-6 (i.e. "ω-6" or "n-6") polyunsaturated fatty acid. Each capsule is film coated with Eudragit® NE 30-D which is a neutral polyacrylate material comprising poly(ethylacrylate-methylmethacrylate) having an average molecular weight of about 800,000. The capsules pass through the stomach and disintegrate to release the contents in the small intestine. Results indicate that clinical relapses in Crohn's disease may be prevented by the oral administration of such coated capsules.

It is disclosed in U.S. Pat. No. 2,870,062A (Scherer et al; published on 20 Jan. 1959) that "standard gelatin capsules" disintegrate in contact with deliquescent or hygroscopic chemicals, such as liquid non-ionic detergents, salts of strong acids and bases, choline chloride and chloral hydrate, encapsulated within. U.S. Pat. No. 2,870,062A discloses the use of capsules made from specially selected low viscosity, high Bloom strength gelatin prepared from acid treated bone precursor. Such capsules do not appear to disintegrate when left in contact with deliquescent or hygroscopic chemicals.

EP0100052A (Yu; published on 8 Feb. 1984) discloses soft gelatin capsules containing PGE-type prostaglandin fatty acid compositions. Comparative studies appear to indicate that soft gelatin capsules made from Type B gelatin accelerate degradation of the prostaglandin composition whereas soft gelatin capsules made from Type A gelatin retain the stabilising effect of the solvent in which the prostaglandin fatty acids are dissolved.

U.S. Pat. No. 6,234,464B (Krumbholz et al; published on 22 May 2001) discloses microencapsulated unsaturated fatty acids or fatty acid compounds or mixtures thereof. The wall of the microcapsules comprises two layers. The inner layer is composed of bone gelatin (gelatin A or gelatin B), casein or an alginate or by a derivative or salt thereof and the outer layer is composed of gelatin B, gum arabic, pectin or chitosan or a derivative or salt thereof. The unsaturated fatty acid may be an omega-3 fatty acid or and ethyl ester or glyceride thereof. U.S. Pat. No. 6,234,464A exemplifies microencapsulated 95% EPA ethyl ester in which the wall of each microcapsule comprises an inner/outer layer combination of gelatin A/gum arabic, gelatin A/pectin or gelatin A/gelatin B.

WO2005/079853A (Buser et al; published 1 Sep. 2005) exemplifies a soft gelatin capsule containing a free fatty acid formulation comprising EPA in free acid form in an amount from 50 wt % to 60 wt % of the formulation, together with DHA in free acid form in an amount from 20 wt % to 30 wt % of the formulation. The gelatin component in the gelatin shell is porcine Type A gelatin. The reference discloses that soft gelatin capsules containing free fatty acids in which the gelatin component in the capsule shell is Type B gelatin can harden over time, and that such hardening increases the disintegration time of the capsules and reduces their shelf life. The data presented in the reference demonstrates that, unlike the soft bovine Type B gelatin capsules, the disintegration time of the soft porcine Type A gelatin capsules does not increase significantly over the period of time measured, and therefore the shelf life of the capsules is improved by using porcine Type A gelatin in place of bovine Type B gelatin.

It has now been suggested (see, for example, US2013/0177643A) that the omega-3 polyunsaturated fatty acid, cis-7,10,13,16,19-docosapentaenoic acid (C22:5 n-3; "DPA" also known as clupodonic acid) may have a significant influence on the therapeutic effectiveness of omega-3 fatty acids derived from fish oils. However, the Inventor anticipates that the free acid form of DPA will cause hardening of a soft gelatin capsule in which the gelatin component in the capsule shell is Type B gelatin.

According to a first aspect of the present invention, there is provided a soft gelatin capsule comprising a soft gelatin shell encapsulating a pharmaceutical formulation, said formulation comprising cis-5,8,11,14,17-eicosapentaenoic acid (C20:5 n-3; "EPA") in free acid form in an amount from 25 wt % to 99 wt % of the formulation and cis-7,10,13,16,19-docosapentaenoic acid (C22:5 n-3; "DPA") in free acid form in an amount from 1 wt % to 75 wt % of the formulation, wherein said shell comprises a gelatin component made up of porcine Type A gelatin and at least one other gelatin, said porcine Type A gelatin being present in an amount of no more than about 75 wt % of said gelatin component.

The porcine Type A gelatin is usually present in an amount of no more than about 70 wt %, e.g. no more than 65 wt %, of the gelatin component. In certain embodiments, the porcine Type A gelatin is present in an amount of no more than about 60 wt %, e.g. no more than about 55 wt %, of the gelatin component. In certain embodiments, the porcine Type A gelatin is present in no more than about 50 wt %, e.g. no more than about 45 wt % or no more than about 40 wt %, of said gelatin component.

The porcine Type A gelatin is usually present in an amount of no less than about 10 wt %, e.g. no less than about 15 wt % or no less than about 20 wt %, of said gelatin component. In certain embodiments, the porcine Type A gelatin is present in no less than about 25 wt %.

The gelatin component comprises at least one other gelatin which may be selected from other Type A gelatins, e.g. bovine Type A and fish Type A gelatin, and Type B gelatins. Preferably, at least one other gelatin is a Type B gelatin.

The gelatin component is preferably a binary mixture of a Type B gelatin and the porcine Type A gelatin.

The Type B gelatin may be from any suitable source but is preferably bovine Type B gelatin.

The DPA in free acid form is usually present in the formulation in an amount of at least 2 wt %, e.g. at least 3 wt %, or at least 4 wt %, of the formulation.

The DPA in free acid form is usually present in the formulation in an amount of no more than about 50 wt %, e.g. no more than about 25 wt %, of the formulation. In certain embodiments, the DPA in free acid form is present in the formulation in an amount of no more than about 10 wt %, e.g. no more than about 8 wt %, of the formulation.

In certain embodiments, the DPA in free acid form is present in the formulation in an amount from about 3 wt % to about 7 wt %, e.g. in an amount from about 4 wt % to about 6 wt %, of the formulation.

The EPA in free acid form is typically present in the formulation in an amount from about 45 wt % to 99 wt %, e.g. in an amount from about 45 wt % to about 65 wt %, of the formulation.

The formulation typically comprises DHA in free acid form in an amount from about 15 wt % to about 25 wt % of said formulation.

In certain embodiments, the formulation comprises EPA in free acid form and DHA in free acid form in a total combined amount from about 60 wt % to about 90 wt % of the formulation.

The formulation typically comprises at least one further omega-3 polyunsaturated fatty acid ("PUFA") in free acid form. The at least one further omega-3 PUFA is usually selected from α-linolenic acid (C18:3 n-3); moroctic acid (018:4 n-3); eicosatetraenoic acid (C20:4 n-3); heneicosapentaenoic acid (C21:5 n-3); and eicosatrienoic acid (C20:3 n-3). In certain embodiments, all of these further free omega-3 PUFAs are present in the formulation.

The total combined amount of omega-3 PUFAs in free acid form in the formulation is preferably from about 80 wt % to about 95 wt % of the formulation.

The formulation also typically comprises at least one omega-6 PUFA in free acid form. The at least one omega-6 PUFA is usually selected from di-homo-gamma-linolenic acid (C20:3 n-6); arachidonic acid (020:4 n-6); linoleic acid (018:2 n-6); docosapentaenoic acid (C22:5; n-6); gamma-linolenic acid (018:3 n-6); and eicosadienoic acid (C22:2 n-6). All of these free omega-6 PUFAs may be present in the formulation.

The total combined amount of omega-6 PUFA(s) in free acid form in the formulation is typically no more than 10 wt % of the formulation.

In preferred embodiments, the formulation is a refined and concentrated fish oil product. The following is an example of a suitable formulation for encapsulation to form the soft gelatin capsules of the present invention (all in free acid form):

| PUFA species (common name) | PUFA species (presumptive identity) | Amount (wt %) (final free acid formulation) |
|---|---|---|
| linoleic acid | 18:2 n-6 | 0.55 |
| gamma-linolenic acid | 18:3 n-6 | 0.15 |
| α-linolenic acid | 18:3 n-3 | 0.39 |
| moroctic acid | 18:4 n-3 | 1.70 |
| eicosadienoic acid | 20:2 n-6 | 0.10 |
| dihomo-gamma-linolenic acid | 20:3 n-6 | 0.35 |
| arachidonic acid | 20:4 n-6 | 2.43 |
| eicosatrienoic acid | 20:3 n-3 | 0.15 |
| eicosatetraenoic acid | 20:4 n-3 | 2.18 |
| EPA | 20:5 n-3 | 57.25 |
| heneicosapentaenoic acid | 21:5 n-3 | 2.79 |
| docosapentaenoic acid | 22:5 n-6 | 0.83 |
| DPA | 22:5 n-3 | 6.23 |
| DHA | 22:6 n-3 | 19.58 |
| | Total % | 98.43 |
| | PUFAs % | 96.30 |
| | Total omega-3 | 90.26 |
| | Total omega-6 | 4.41 |
| | Remaining PUFAs | 1.63 |
| | Saturates % | 0.35 |
| | Mono-saturates % | 1.34 |
| | Unknowns % | 0.42 |

Suitable processes for producing formulations for encapsulation in soft gelatin capsules according to the present invention are described in U.S. Ser. No. 13/734,846 filed on 4 Jan. 2013, published as US2013/0177643A1 on 11 Jul. 2013 and claiming the benefit of US provisional patent application Nos. 61/583,796 filed on 6 Jan. 2012, 61/664,047 filed on 25 Jun. 2012, 61/669,940 filed on 10 Jul. 2012, 61/680,622 filed on 7 Aug. 2012, 61/710,517 filed on 5 Oct. 2012 and 61/713,388 filed on 12 Oct. 2012.

The formulation usually comprises an antioxidant such as butylated hydroxyanisole ("BHA") or α-tocopherol. The antioxidant is usually present in an amount from about 0.2 wt % to about 0.4 wt % of the formulation.

The soft gelatin capsule is not a microcapsule. In this connection, the soft gelatin capsule typically encapsulates from about 100 mg to about 2000 mg of the formulation. In some embodiments, the capsule contains about 500 mg of the formulation. Such embodiments may be intended for administration to children. In other embodiments, the capsule contains about 1000 mg of the formulation. Such other embodiments may be intended for administration to adults.

Release of the formulation from the soft gelatin capsule is usually controlled to occur primarily along at least a significant portion of the small intestine. In this connection, the soft gelatin capsule may be coated with a polymeric film coating to control release of the formulation in the intestines. Initial release is preferably post-gastric with the bulk (e.g. at least 50%, preferably at least 60% and more preferably at least 75%) of the formulation being released in the ileum. Release is preferably sustained, e.g. in a microdrop-wise manner.

The polymeric film coating may provide time- (but not pH-) controlled release of the formulation. An example of a film forming polymeric material suitable for providing time- (but not pH-) controlled release of the formulation would be a neutral polyacrylate coating such as Eudragit® NE 30D. Release from such a coating is sustained in a microdrop-wise manner.

In the alternative, the polymeric film coating may provide pH-controlled release of the formulation. Such polymeric materials are known as enteric polymers. Examples of suitable enteric polymers include cellulose acetate phthalate (CAP), cellulose acetate trimellitate (CAT), hydroxypropylmethylcellulose acetate succinate (HPMC-AS) and anionic poly(meth)acrylate material such as Eudragit® L or Eudragit® S 100.

According to a second aspect of the present invention, there is provided a process for manufacturing a soft gelatin capsule containing a pharmaceutical formulation comprising EPA in free acid form in an amount from 25 wt % to 99 wt % of said formulation and DPA in free acid form in an amount from 1 wt % to 99 wt % of said formulation, said process comprising encapsulating said formulation in a soft gelatin shell comprising a gelatin component made up of porcine Type A gelatin and at least one other gelatin, said porcine Type A gelatin being present in an amount of no more than about 75 wt % of said gelatin component.

Soft gelatin capsules of the present invention may be used in the treatment or prophylaxis of chronic inflammatory conditions such as inflammatory bowel disease (including Crohn's disease, ulcerative colitis and pouchitis), rheumatoid arthritis, psoriasis or Behçet's syndrome; hyperlipidaemia or hypertriglyceridaemia; asthma; bipolar disorder; and neoplastic disease such as prostate cancer or bowel cancer.

In certain preferred embodiments, the soft gelatin capsules will be used to treat or prevent hyperlipidaemia or hypertriglyceridaemia. In particular, the capsules will be used to treat patients having "moderate" hypertriglyceridaemia, i.e. patients having a blood plasma triglyceride level from about 200 to about 500 mg/dl, who are also on statin therapy, and patients having "severe" hypertriglyceridaemia, i.e. patients having a blood plasma triglyceride level of at least 500 mg/dl.

In addition, the capsules may be used to treat or prevent IBD, or to prevent post-operative recurrence of Crohn's disease.

According to a third aspect of the present invention, there is provided use of a pharmaceutical formulation comprising EPA in free acid form in an amount from 25 wt % to 99 wt % of said formulation and DPA in free acid form in an amount from 1 wt % to 99 wt % of said formulation in the manufacture of a medicament comprising a soft gelatin capsule, said capsule comprising a soft gelatin shell encapsulating said pharmaceutical formulation, said shell comprising a gelatin component made up of porcine Type A gelatin and at least one other gelatin, said porcine Type A gelatin being present in an amount of no more than about 75 wt % of said gelatin component, for the oral treatment or prophylaxis of a condition selected from chronic inflammatory conditions; hyperlipidaemia; hypertriglyceridaemia (moderate or severe); asthma; bipolar disorder; and neoplastic disease. The soft gelatin capsule is usually as defined above.

According to a fourth aspect of the present invention, there is provided a method of treatment or prophylaxis of a condition selected from chronic inflammatory conditions; hyperlipidaemia; hypertriglyceridaemia (moderate or severe); asthma; bipolar disorder; and neoplastic disease, said method comprising administering a therapeutically effective amount of a pharmaceutical formulation comprising EPA in free acid form in an amount from 25 wt % to 99 wt % of said formulation and DPA in free acid form in an amount from 1 wt % to 99 wt % of said formulation, in the form of a plurality of soft gelatin capsules, each capsule comprising a soft gelatin shell encapsulating said formulation, wherein said shell comprises a gelatin component made up of porcine Type A gelatin and at least one other gelatin, said porcine Type A gelatin being present in an amount of no more than 75 wt % of said gelatin component. The soft gelatin capsule is usually as defined above.

The following is a description, by way of example only, of a presently preferred embodiment of the present invention.

Soft gelatin capsules according to the present invention are produced using a standard rotary die method involving conventional equipment operating under standard parameters and conditions.

EXAMPLE 1

Porcine Type A gelatin powder and bovine Type B gelatin powder are mixed in equal proportions by weight to produce a gelatin component powder. The gelatin component powder is mixed with water and the plasticisers, glycerol and sorbitol, and the mixture is heated to form a molten gelatin mass. Two thin ribbons of the molten gelatin are produced and passed between two die rolls which determine the shape and size of the capsules. The formulation as described in Table 1 above (and containing α-tocopherol in an amount of 0.3 wt % of the resultant formulation) is injected between the two gelatin ribbons just before the die rolls seal the two sides of the capsule shell together to form the soft gelatin capsule. The resultant capsules are then dried (28 h @ 25° C./20% rH) to the required moisture content.

The composition of the finished capsules is about 62 wt % gelatin component (50% porcine Type A gelatin; 50% bovine Type B gelatin), about 23 wt % glycerol, about 5 wt % sorbitol. The moisture content of the capsules (as measured by loss on drying; 15 h @ 105° C.) is about 10 wt %.

EXAMPLE 2

Porcine Type A gelatin powder and bovine Type B gelatin powder are mixed to produce a gelatin component powder having a ratio by weight of porcine Type A gelatin to bovine Type B gelatin of 1:2. The gelatin component powder is mixed with water and the plasticisers, glycerol and sorbitol, and the mixture is heated to form a molten gelatin mass. Two thin ribbons of the molten gelatin are produced and passed between two die rolls which determine the shape and size of the capsules. The formulation as described in Table 1 above (and containing α-tocopherol in an amount of 0.3 wt % of the resultant formulation) is injected between the two gelatin ribbons just before the die rolls seal the two sides of the capsule shell together to form the soft gelatin capsule. The resultant capsules are then dried (28 h @ 25° C./20% rH) to the required moisture content.

The composition of the finished capsules is about 62 wt % gelatin component (33% porcine Type A gelatin; 67% bovine Type B gelatin), about 23 wt % glycerol, about 5 wt % sorbitol. The moisture content of the capsules (as measured by loss on drying; 15 h @ 105° C.) is about 10 wt %.

It will be appreciated that the invention is not restricted to the details described above with reference to the preferred embodiments but that numerous modifications and variations can be made without departing from the spirit or scope of the invention as defined by the following claims.

The invention claimed is:

1. A soft gelatin capsule, comprising:
   a soft gelatin shell encapsulating a pharmaceutical formulation,
   wherein the pharmaceutical formulation comprises the following components all in free acid form:
   0.55 wt % of linoleic acid;
   0.15 wt % of gamma-linolenic acid;
   0.39 wt % of α-linolenic acid;
   1.70 wt % of moroctic acid;
   0.10 wt % of eicosadienoic acid;
   0.35 wt % of dihomo-gamma-linolenic acid;
   2.43 wt % arachidonic acid;
   0.15 wt % of eicosatrienoic acid;
   2.18 wt % of eicosatetraenoic acid;
   57.25 wt % of cis-5,8,11,14,17-eicosapentaenoic acid (C20:5 n-3; "EPA");
   2.79 wt % of heneicosapentaenoic acid;
   0.83 wt % of docosapentaenoic acid;
   6.23 wt % of cis-7,10,13,16,19-docosapentaenoic acid (C22:5 n-3; "DPA"); and
   19.58 wt % of cis-4,7,10,13,16,19-docosahexaenoic acid (C22:6 n-3; "DHA");
   wherein the soft gelatin shell comprises a gelatin component made up of porcine Type A gelatin and a Type B gelatin; and
   wherein the porcine Type A gelatin is present in an amount of no more than about 75 wt % of the gelatin component.

2. The soft gelatin capsule as claimed in claim 1, wherein the porcine Type A gelatin is present in an amount of no more than about 50 wt % of said gelatin component.

3. The soft gelatin capsule as claimed in claim 1, wherein the porcine Type A gelatin is present in an amount of no less than about 10 wt % of the gelatin component.

4. The soft gelatin capsule as claimed in claim 1, wherein the porcine Type A gelatin is present in an amount of no less than about 25 wt % of the gelatin component.

5. The soft gelatin capsule as claimed in claim 1, wherein the Type B gelatin is bovine Type B gelatin.

6. The soft gelatin capsule as claimed in claim 1, encapsulating from about 100 mg to about 2000 mg of the pharmaceutical formulation.

7. The soft gelatin capsule as claimed in claim 1, wherein the capsule is coated with a polymeric film coating to control release of the pharmaceutical formulation in the intestines.

8. A process for manufacturing a soft gelatin capsule according to claim 1, said process comprising:
   encapsulating said pharmaceutical formulation in said soft gelatin shell.

9. A method of treatment of a condition, said method comprising:
   administering a therapeutically effective amount of at least one soft gelatin capsule according to claim 1 to a subject in need thereof;
   wherein said condition is at least one selected from the group consisting of chronic inflammatory conditions, hyperlipidaemia, hypertriglyceridaemia, asthma, and bipolar disorder.

10. The soft gelatin capsule as claimed in claim 1, wherein the porcine Type A gelatin is present in an amount of no less than about 10 wt % to no more than about 75 wt % of the gelatin component.

11. The soft gelatin capsule as claimed in claim 1, wherein the porcine Type A gelatin is present in an amount of no less than about 0.5 wt % to no more than about 75 wt % of the gelatin component.

* * * * *

UNITED STATES PATENT AND TRADEMARK OFFICE
CERTIFICATE OF CORRECTION

PATENT NO. : 10,314,789 B2
APPLICATION NO. : 14/427846
DATED : June 11, 2019
INVENTOR(S) : Johannes Spleiss Page 1 of 1

It is certified that error appears in the above-identified patent and that said Letters Patent is hereby corrected as shown below:

On the Title Page

Item (71) the Applicant is currently:
"Chrysalis Pharma AG, Sachsein (CH)"
And should be:
--Chrysalis Pharma AG, Sachseln (CH)--

Signed and Sealed this
Twentieth Day of August, 2019

Andrei Iancu
*Director of the United States Patent and Trademark Office*